United States Patent [19]

Parris et al.

[11] Patent Number: 4,900,832

[45] Date of Patent: Feb. 13, 1990

[54] PROCESS FOR THE CATALYTIC AMINATION OF ALCOHOLS AND DIOLS USING NON-ACIDIC HYDROXYAPATITE CATALYSTS

[75] Inventors: Gene E. Parris, Revere; Ronald Pierantozzi, Orefield, both of Pa.

[73] Assignee: Air Products and Chemicals, Inc., Allentown, Pa.

[21] Appl. No.: 227,569

[22] Filed: Aug. 2, 1988

[51] Int. Cl.$^4$ .................. C07D 211/14; C07D 401/06; C07C 85/06
[52] U.S. Cl. ..................................... 546/186; 546/184; 564/402; 564/184; 564/186
[58] Field of Search ........................ 564/479, 480, 402; 546/184, 186

[56] References Cited

U.S. PATENT DOCUMENTS

| | | | |
|---|---|---|---|
| 4,049,657 | 9/1977 | Brennan et al. | 544/402 |
| 4,082,805 | 4/1978 | Kaeding | 564/402 |
| 4,117,227 | 9/1978 | Brennan | 544/170 |
| 4,501,889 | 2/1985 | Wells et al. | 544/106 |
| 4,582,904 | 4/1986 | Wells et al. | 546/184 |

*Primary Examiner*—Robert T. Bond
*Attorney, Agent, or Firm*—Keith D. Gourley; James C. Simmons; William F. Marsh

[57] ABSTRACT

The present invention relates to a process for the catalytic amination of 1° and 2° alcohols and diols wherein an amine is reacted with an alcohol or diol in the presence of a non-acidic cationic hydroxyapatite catalyst. A typical reaction includes the amination of ethanol with piperidine to form N-ethylpiperidine. The hydroxyapatite catalyst provides high conversion and selectivity toward the N-alkylated product. Product selectivity can be controlled by adjusting the ratio of cation to phosphorus in the hydroxyapatite catalyst.

13 Claims, No Drawings

PROCESS FOR THE CATALYTIC AMINATION OF ALCOHOLS AND DIOLS USING NON-ACIDIC HYDROXYAPATITE CATALYSTS

TECHNICAL FIELD OF THE INVENTION

The present invention relates to a process for the catalytic amination of alcohols and diols using non-acidic cationic hydroxyapatite catalysts.

BACKGROUND OF THE INVENTION

Current processes for amination of alcohols and/or diols typically employ heterogeneous catalysts which comprise supported transition metals with known hydrogenation/dehydrogenaton activity and/or acidic compositions such as zeolites, mixed oxides, and metal phosphates. Catalysts containing transition metals typically yield by-product amines and olefinic amines which deactivate the catalyst and often produce undesirable aldehyde-type by-products. Acidic catalysts are usually non-selective for alcohol amination reactions and yield the corresponding ether, unsaturated hydrocarbon, polymeric product and scrambled amines as by-products via transalkylation and disproportionation reactions.

Synthetic methods heretofore utilized for production of aliphatic and aromatic amines include amination of alcohols with ammonia/amines in the presence of hydrogenation/dehydrogenation catalysts, amination of alcohols with ammonia/amines using acidic dehydration-type catalysts and reductive amination of aldehydes and ketones over transition metal catalysts.

However, such catalysts tend to dehydrate alcohols to form olefin or ether by-products thereby reducing the yield of the desired amination product. To avoid high alkene formation which promotes catalyst deactivation, acidic catalysts are typically operated at lower temperatures. Unfortunately, lower reaction temperatures reduce reaction efficiency because lower amine/alcohol ratios are required to achieve high amine conversion. Additionally, both acidic and dehydrogenation-type catalysts inherently require some recycle of unconverted reactants.

Several acid metal phosphate catalysts, particularly phosphates of boron, aluminum and trivalent iron, have been proposed for use in intramolecular cyclic dehydration reactions and other condensation reactions involving amine compounds. Examples of such reactions are found in U.S. Pat. No. 4,117,227, which discloses conversion of an N-substituted diethanolamine to the corresponding N-substituted morpholine. Additionally. U.S. Pat. No. 4,049,657 discloses reaction of piperidine with ethanolamine over metal phosphate catalysts to produce N-aminoethyl piperidine.

U.S. Pat. No. 4,082,805 relates to a process for the production of aliphatic amines by reacting a $C_1$ to $C_5$ alcohol or ether with ammonia in the presence of a crystalline aluminosilicate catalyst having the structure of ZSM-5, ZSM-11 or ZSM-21. Preferred catalysts have a high silica to alumina ratio, typically greater than 5 and preferably greater than 30. The reaction is effected at a temperature between 300° C. and about 500° C. a pressure between atmospheric and 1000 psig with the relative feed rates, expressed in grams per hour of alcohol or ether to ammonia within the approximate range of 1:1 to about 5:1.

U.S. Pat. 4,501,889, assigned to Air Products and Chemicals, Inc. discloses a process for preparing morpholine compounds by reacting 2-(2-aminoethoxy)ethanol in the presence of a catalyst selected from the group consisting of the pyrophosphate. monohydrogen phosphate and dihydrogen phosphate of strontium, copper, magnesium, calcium, barium, zinc, aluminum, lanthanum, cobalt, nickel, cerium and neodymium and mixtures thereof. Preferred catalysts are the soluble metal salts of strong acids such as metal nitrates in substantially stoichiometric proportion to the phosphate.

BRIEF SUMMARY OF THE INVENTION

This invention relates to a process for the amination of 1° and 2° alcohols and diols wherein non-acidic cationic hydroxyapatites are employed as catalysts. Use of cationic hydroxyapatite catalysts in reactions such as the amination of ethanol with piperidine to form N-ethylpiperidine afford very high selectivity thereby reducing costs associated with separation and purification of complex reaction product mixtures. Product selectivity can be controlled by adjusting the ratio of cation to phosphorus in the catalyst.

The non-acidic hydroxyapatite catalysts of the present invention have the formula

$$M_x^a(PO_4)_y(OH)_z$$

wherein $M^a$ is a cation selected from the group consisting of $Ca^{2+}$, $Mg^{2+}$, $Sr^{2+}$, $La^{3+}$, $Ce^{3+}$, $Fe^{2+}$, $Cu^{2+}$, $Zn^{2+}$, $Al^{3+}$, $B^{3+}$ and $Ga^{3+}$ and wherein the cation to phosphorus ratio, x/y, ranges from about 1.3 to about 2.4 when a is 2+ and from about 0.87 to about 1.6 when a is 3+ and the ratio of z/y is about 0.33 to about 1.8 when a is 2+ and from about 1.0 to about 3.0 when a is 3+.

A preferred embodiment of the invention is a calcium hydroxyapatite catalyst having the structural formula

$$Ca_x^{2+}(PO_4)_y(OH)_z$$

wherein the ratio of x/y is between about 1.67 and about 2.4 and the ratio of z/y is between about 0.33 and 1.8. The x/y ratio may additionally range from about 1.3 to about 1.67 providing the hydroxyapatite catalyst is calcined at about 350° C. to 650° C. for a sufficient time to render the catalyst non acidic. Such catalysts may additionally contain up to about 5 wt. % of an alkali ion selected from the group consisting of lithium, sodium, potassium. rubidum or cesium.

The reaction is conducted in the presence of an effective amount of hydroxyapatite catalyst and at a temperature sufficient to effect a reaction between the alcohol or diol and the aminating agent to produce the corresponding alkyl or arylamine product. Typical reaction temperatures range from about 150° to 500° C., preferably from about 200° to 400° C.

DETAILED DESCRIPTION OF THE INVENTION

This invention is directed to a process for the catalytic amination of 1° and 2° alcohols and diols wherein non-acidic cationic hydroxyapatites are employed as catalysts. Hydroxyapatites are phosphate minerals having a hexagonal crystal structure which can accommodate a wide variety of chemical structures within the crystal lattice. The stable hexagonal structure is unique to these phosphate systems and affords good hydrothermal stability. Additionally, these catalysts can be used in liquid phase reactions without dissolving in the reaction medium. As such, these amination catalysts differ significantly from phosphates taught in the prior art.

Hydroxyapatites suitable for practicing the invention are represented by the structural formula

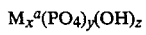

wherein the cation to phosphorus ratio, x/y, ranges from about 1.3 to about 2.4 when a is 2+ and from about 0.87 to about 1.6 when a is 3+ and the ratio of z/y is about 0.33 to about 1.8 when a is 2+ and from about 1.0 to about 3.0 when a is 3+. The catalyst may additionally contain up to about 5 wt. % of a monovalent alkali ion selected from the group consisting of lithium. sodium, potassium, rubidium or cesium. Hydroxyapatite catalysts of the claimed invention can be prepared with varying cation to phosphorus ratios in order to maximize product selectivity.

Another embodiment of the present invention relates to a catalyst having the above-mentioned formula wherein the cation is a mixture of cations selected from the group consisting of $Ca^{2+}$, $Mg^{2+}$, $Sr^{2+}$, $La^{3+}$, $Ce^{3+}$, $Fe^{2+}$, $Cu^{2+}$, $Zn^{2+}$, $Al^{2+}$, $B^{3+}$ and $Ga^{3+}$ wherein at least 50% of the cation content comprises a mixture of two or more of the enumerated cations.

A preferred embodiment of this invention is a calcium hydroxyapatite catalyst having the structural formula

wherein the ratio of x/y is between about 1.3 and about 2.4 and the ratio of z/y is between about 0.33 and 1.8. This catalyst may additionally contain up to about 5 wt. % of an alkali ion selected from the group consisting of lithium, sodium, potassium, rubidium or cesium. Preferred calcium hydroxyapatite catalysts have a cation/phosphorus ratio of greater than or equal to 1.67. Optionally hydroxyapatite catalysts having a cation/phosphorus ratio of between about 1.3 and 1.67 must be calcined in the temperature range of about 350° to about 650° C. to produce non-acidic catalysts.

The process for aminating 1° and 2° alcohols and diols is conducted in the presence of an effective amount of a hydroxyapatite catalyst and at a temperature sufficient to effect reaction between the alcohol or diol and the aminating agent to produce the desired corresponding alkyl or arylamine product. Typical reaction temperatures range from about 150° to 500° C., preferably from about 200° to 400° C.

It shall be understood that when alcohols are discussed, the invention contemplates the use of diols. Suitable alcohols are $C_1$-$C_{10}$ linear and branched acyclic, cyclic and aromatic alcohols including but not limited to methanol, ethanol. isopropanol. ethylene glycol, benzyl alcohol, butanediol and para-xyleneglycol.

Suitable aminating agents include ammonia and 1° and 2° aliphatic and aromatic amines. Such 1° and 2° amines may vary broadly in structure and their use in amination reactions is limited only by their solubility in the gaseous or liquid reaction medium. Preferred aminating agents include methylamine. ethylamine, piperidine, diethylamine and aniline.

The process of this invention may take place in a liquid phase reaction or a gas phase reaction. Temperatures from about 150° to 500° C. and pressures from about 1 to 100 atmospheres are contemplated when employing the catalysts in a gas phase reaction. The pressure utilized in carrying out liquid phase reactions is that pressure sufficient to maintain the reactants in essentially the liquid phase although higher pressures may be used. Liquid phase reaction temperatures may range from about 150° to 400° C. When utilizing these temperatures and pressures, the reaction is allowed to proceed until a desired conversion to product is obtained or the reaction is complete.

The quantity of hydroxyapatite catalyst used in the reaction is empirical and can vary widely depending upon catalyst and reactant reactivity. An effective amount of hydroxyapatite catalyst is used; i.e., an amount sufficient to cause a reaction between the alcohol and the amine to yield the desired N alkylated amine product at the temperature and pressure used. The amount of active hydroxyapatite catalyst used to provide a catalytic effect in fixed or continuous bed reaction systems typically ranges from about 0.05 to 20 mole % based upon the amount of aminating agent present in the reaction mixture and preferably ranges from about 0.5 to 4 mole %. However, the amount of catalyst to be used is empirical and is adjusted depending on the particular reaction since the amine products may be generated in an equilibrium distribution.

For a continuous reaction using a fixed bed system in which the hydroxyapatite catalyst is present in conjunction with an inert support or in bulk form, suitable reaction temperatures range from 150° to 500° C. preferably 200° to 400° C. and suitable pressures range from 1 to 100 atmospheres, preferably 10 to 30 atmospheres. Flow rates, expressed as liquid hourly space velocity (LHSV), range from about 0.1 to 4 $hour^{-1}$ based on the aminating agent being used.

The mole ratio of amine to alcohol reactants ranges typically from about 1:3 to 20:1. and preferably ranges from about 1:1 to 10:1. The process may advantageously be carried out by regulating the proportion of aminating agent to alcohol such that a stoichiometric excess of aminating agent is used, e.g. from about 1.1:1 to a 20:1 ratio of aminating agent to alcohol which results in formation of predominantly the desired amination product.

Hydroxyapatite catalysts may be employed in the form of irregular particles of the desired size range prepared by breaking up the washed and dried filter cake or in the form of regular shaped pellets obtained by known methods of casting or extruding. The hydroxyapatite catalyst may also be deposited on, or into the pores of a porous substrate by known synthetic methods.

The process of the invention can be carried out batch wise or continuously by employing well known batch and continuous processing techniques and conventional processing apparatus which utilize catalysts in the form of pellets, extrudates, powders, etc. In such continuous reaction processes, the above-described hydroxyapatite catalysts may be employed as a feed stream alone or admixed with a reactant feed stream, or they may be employed as a fixed bed catalyst in a continuous reactor system. Generally, suitable fixed bed catalysts comprise the hydroxyapatite supported on a reactor packing material such as silica, silica-alumina, alumina, porous glass or diatomaceous earth. Such fixed bed supported catalysts and procedures for their preparation are well known in the art and many are readily available commercially.

Recovery of the desired amination product from the reaction mixture can be accomplished by conventional techniques including but not limited to a fractionation step such as distillation. A particular advantage in practicing this invention relates to the simplified separation and purification steps required to isolate the desired products based upon the high product selectivity afforded by hydroxyapatite catalysts.

Overall acidity of the subject catalysts may be effectively controlled by varying the catalyst cation to phosphorus ratio which is believed to alter the density of reaction centers on the catalyst surface. For example, an increase in the cation/phosphorus ratio renders the hydroxyapatite catalyst surface more basic. Oligomerization side-reactions can be reduced particularly when the alcohol reactant is a diol by decreasing the density of reaction centers on the catalyst surface.

At calcium/phosphorus ratios greater than 1.67, it is believed that the hydroxyapatite structure incorporates $Ca(OH)_2$ which may physically decrease the number of $PO_4^{3-}$ adsorption/reaction centers on the catalyst surface. When the Ca/P ratio is less than 1.67, the catalyst must be pre-calcined or treated with steam, preferably in-situ to remove any residual acidity. This step is believed to convert acidic $HPO_4^{2-}$ groups to the anhydride $P_2O_7^{4-}$ via a dehydration mechanism.

An alternate method for deacidifying hydroxyapatite catalysts having a cation/phosphorus ratio less that 1.67 contemplates treatment of the dried catalyst with a dilute base solution. The base may be an inorganic base or an organic base. Typical bases which can be employed include sodium hydroxide and other bases known in the art for modifying the pH of solutions. The concentration of added base should be such as not to raise the pH of the catalyst to an undesirably high level which could affect the crystallinity of the hydroxyapatite catalyst undergoing treatment. Typically, a 0.1–0.3 molar base solution in used.

The process for aminating alcohols over non-acidic hydroxyapatite catalysts selectively produces the corresponding alkylor arylamine. The process is highly selective toward formation of mono- and/or di-aminated products prepared from both aliphatic and aromatic amines when the alcohol employed is a diol. The relative amounts of secondary versus tertiary and mono- verses di-aminated products can be controlled to a certain extent by adjusting the reaction temperature to optimize desired product formation. Catalytic amination of alcohols and diols in the presence of hydroxyapatite catalysts also eliminates the need to co-feed hydrogen into the reaction process and provides stable catalyst performance.

Reaction products obtained by this process may be a mixture of primary, secondary and tertiary aliphatic or aromatic amines which can either be collected as a combined amine product or separated into their respective components. In general, the secondary and tertiary amines comprise a smaller fraction of the reaction products as the size and molecular weight of the alcohol or diol reactant increases.

In using catalysts of the present invention to aminate alcohols, substantially the same conditions may be employed as when using known amination catalysts for the particular synthesis. For optimum results, however, some adjustment in the temperature. diluent and/or space velocity may be found beneficial.

The following examples illustrate the preparation of catalysts used to practice the present process and are not intended to limit the scope of the invention.

EXAMPLE 1

Preparation of a Calcium Hydroxyapatite Catalyst Having a Ca/P Ratio of 1.7

This example illustrates preparation of a calcium hydroxyapatite catalyst. 177.2 g $Ca(NO_3)_2 \cdot 4H_2O$ was dissolved in deionized $H_2O$, diluted to 1 L, and the pH was adjusted to 10.5 with $NH_4OH$ solution. In a separate 2 L round bottom flask 33.0 g $(NH_4)_2HPO_4$ was dissolved in deionized $H_2O$, diluted to 1 L and adjusted to pH=10.5 with $NH_4OH$ solution to a final volume of 1.5 L. In a 5 L round bottom flask was placed 0.55 L of the $Ca(NO_3)_2$ solution to which the $(NH_4)_2HPO_4$ solution was added with stirring over a two minute period. A white precipitate formed which was isolated by vacuum filtration. The precipitate was washed 3 times with deionized $H_2O$ to a final pH of 7.7 prior to being dried in an oven at 105° C. Analytical: Ca=43.4 wt. %. Cu less than 5 ppm and P=19.9 wt. %. The Ca/P ratio was 1.7.

EXAMPLE 2

Preparation of a Calcium Hydroxyapatite Catalyst Having a Ca/P Ratio of 1.7

This example illustrates preparation of another calcium hydroxyapatite catalyst. 0.21 L of 85% phosphoric acid was diluted to 1 L with deionized $H_2O$ to make a 3.11 m H solution. In a 5 L flask 138.2 g $Ca(OH)_2$ was added rapidly to 1.5 L deionized $H_2O$ and mixed thoroughly. To this solution was added over five mins. 0.41 L of the 3.11 m $H_3PO_4$ with continuous stirring for an additional 0.5 hr. Additional $Ca(OH)_2$ in the amount of 22.4 g was then added over 5 mns. and the contents stirred for another 1 hr. The resulting precipitate was washed twice with 1.4 L deionized $H_2O$ each to a final pH of 6.7. The white solid was dried at 110° C. Analytical: Ca=34.8 wt. %. Cu less than 5 ppm; P=15.8 wt. %. The Ca/P ratio was 1.7.

EXAMPLE 3

Preparation of a Calcium Hydroxyapatite Catalyst Having a Ca/P Ratio of 1.6

This example illustrates the preparation of a calcium hydroxyapatite catalyst similar to example 2. 0.21 L of 85% phosphoric acid was diluted to 1 L with deionized $H_2O$ to make a 3.11 m $H_3PO_4$ solution. In a 5 L flask 138.2 g $Ca(OH)_2$ was added rapidly to 1.5 L deionized $H_2O$ and mixed thoroughly. To this solution was added 0.41 L of the 3.11 m $H_3PO_4$ over 5 mins. with continuous stirring for an additional 0.5 hr. Additional $Ca(OH)_2$ in the amount of 9.7 g was added over 5 mins. and the contents stirred for another 1 hr. The pH after the second wash with deionized $H_2O$ was 6.5. Analytical: Ca=39.0 wt. %. Cu less than 5 ppm; P=18.9 wt. %. The Ca/P ratio was 1.6.

EXAMPLE 4

Preparation of a Calcium Hydroxyapatite Catalyst Having a Ca/P Ratio of 2.2

This example illustrates yet another preparation of a calcium hydroxyapatite catalyst wherein the calcium/phosphorus ratio is 2.2. The experimental procedure used was similar to that of example 2 except that the additional amount of Ca(OH)₂ added was 90.5 g. Analytical: Ca=38.6 wt. %, Cu less than 5 ppm; P=13.8 wt. %. The Ca/P ratio was 2.2.

EXAMPLE 5

Preparation of a Copper Promoted Calcium Hydroxyapatite Catalyst Having a Ca+Cu/P Ratio of 1.7

This example illustrates preparation of a copper promoted calcium hydroxyapatite catalyst. The experimental procedure used was generally the same as example 1. However, 0.03 L of 0.75 m Cu(NO₃)₂:3H₂O solution was mixed with 0.55 L of Ca(NO₃)₂:4H₂O and the solution adjusted with NH₄OH solution to a pH of 10.5. The precipitate obtained after addition of (NH₄)₂HPO₄ was twice washed to a final pH of 7.9. The blue-purple solid was then washed in anhydrous ethanol and air dried. The solid material contained 0.5 wt. % Cu and had a (Ca+Cu)/P ratio of 1.7. Analytical: Ca=35.6 wt. %. Cu=0.50 wt. % and P=16.5 wt. %.

EXAMPLE 6

Preparation of a Calcium Hydroxyapatite Catalyst Having a Ca/P Ratio of 1.8

This example illustrates yet another preparation of a calcium hydroxyapatite catalyst. The experimental procedure used was similar to that of example 2 except that the additional amount of Ca(OH)z added was 39.7 g. Analytical: Ca=38.9 wt. %. Cu less than 5 ppm; P=17.0 wt. %. The Ca/P ratio was 1.8.

COMPARATIVE EXAMPLE 7

Preparation of a $H_3PO_4/Al_2O_3$ Catalyst

Catapal alumina, 300 g, was placed in a muffle furnace at 500° C. for 8 hours The final dried weight was 214 g. To 161 g of the calcined alumina was added 0.08 L of $H_3PO_4$ solution containing 12.6 g $H_3PO_4$ in deionized $H_2O$. The solid was mixed thoroughly with a mortar and pestle during slow addition of the $H_3PO_4$ solution which incipiently wetted the alumina. The solid was dried at 110° C. for 4 hours. This material contained 1.98 wt. % P.

COMPARATIVE EXAMPLE 8

Preparation of a 4.5% $Cu/Al_2O_3$ Catalyst

This example illustrates preparation of a catalyst comprising 4.6 wt. % Cu on $Al_2O_3$. Catapal alumina was calcined at 480° C. for 4 hours. 19 g of Cu(NO₃)₂:3-H₂O was dissolved in 0.05 L H₂O and mixed thoroughly with 100 g of the calcined alumina powder. The material was dried at 110° C. and calcined at 800° C. for about two hours.

COMPARATIVE EXAMPLE 9

Preparation of an $AlPO_4$ Catalyst

This example illustrates preparation of an $AlPO_4$ catalyst. 100 g Al(NO₃)₃:9H₂O and 30.75 g of 85% $H_3PO_4$ were mixed into 0.75 L $H_2O$. 94.5 g of NH₄OH was added to 0.2 L H₂O and the mixture added slowly to the phosphate solution to a final pH of 7.0. The gel obtained was filtered, dispersed in isopropanol, filtered and air dried. The dried solid was calcined at 650° C. for 2 hrs. Elemental: Al/P atomic ratio of 1.0 comprising 23.3 wt. % Al and 26.9 wt. % P.

COMPARATIVE EXAMPLE 10

Preparation of a $H_3PO_4/SiO_2$ Catalyst

A commercially available $H_3PO_4/SiO_2$ catalyst for the amination of alcohols was obtained from Air Products and Chemicals, Inc. The catalyst contained 34 wt. % $H_3PO_4$ on silica and was prepared by spray impregnation of $H_3PO_4$ onto granular Davison grade 59 silica gel. The catalyst had a surface area of 159 m²/g and a bulk density of 0.64 g/ml.

Catalysts prepared according to examples 1 through 10 were tested for catalytic performance in the amination of alcohols and diols. Results for the reaction of piperidine and ethanol, diethylamine and ethanol, aniline and isopropanol and piperidine and ethylene glycol are provided in Tables I through IV. respectively. Examples 13-17 utilize catalysts which were precalcined at the temperatures specified in Table I, prior to conducting the amination of ethanol with piperidine. Examples 20-23, 26 and 33 are comparative using catalysts taught in the art for amination reactions.

TABLE I

| | | | | PiPD | | | | | | Calcination |
| | Catalyst of | | Temp | Conversion | Selectivities (mol %)[b] | | | | | Temp |
| Example | Example | Type | °C. | % | NEP | REP | DREP | DEE | $C_2^=$ | | °C. |
|---|---|---|---|---|---|---|---|---|---|---|
| 11 | 1 | CaHAP-1.7 | 296 | 27 | >99 | — | — | <1 | — | — |
| 12 | 1 | | 350 | 83 | 95 | 1 | — | 1 | 3 | — |
| 13 | 1 | | 350 | 76 | 99 | — | — | <1 | <1 | 450 |
| 14 | 2 | −1.7 | 357 | 84 | 98 | — | — | <1 | <1 | 450 |
| 15 | 3 | −1.6 | 308 | 31 | 99 | — | — | <1 | <1 | 450 |
| 16 | 6 | −1.8 | 303 | 19 | >99 | — | — | — | <1 | 450 |
| 17 | 4 | −2.2 | 306 | 3 | >99 | — | — | — | <1 | 450 |
| 18 | 5 | CaCuHAP-1.7 | 302 | 30 | 84 | 12 | 4 | — | — | — |
| 19 | 5 | | 350 | 69 | 83 | 11 | 4 | 2 | <1 | — |
| 20 | 9 | AlPO₄—1.0 | 358 | 75 | 85 | 1 | 5 | 6 | 3 | 650 |
| 21 | 10 | H₃PO₄/SiO₂ | 355 | 76[c] | 80 | — | — | 4 | 16 | — |
| 22 | 7 | H₃PO₄/Al₂O₃ | 358 | 70 | 83 | 1 | 2 | 12 | 2 | |
| 23 | 8 | 4.5% Cu/Al₂O₃ | 300 | 47 | 54 | 35 | 9 | <1 | — | 800 |

[a]P = 240 psig, PiPD/ETOH feed molar ratio = 1, GHSV = 160h⁻¹
[b]NEP = N—ethylpiperidine; REP = ring substituted ethyl pipD; DREP = Di-ring ethyl pipD; DEE = diethyl ether; $C_2^=$ = ethylene
[c]GHSV = 640 h⁻¹
[d]GHSV = CC feed (STP)/CC catalyst/hr.

TABLE II

Amination of Ethanol with Diethylamine (DEA)[a]

| Example | Catalyst of Example | Type | Temp °C. | DEA Conversion % | Selectivities (mol %)[b] | | | | | GHSV[c] h$^{-1}$ | Pressure psig |
|---|---|---|---|---|---|---|---|---|---|---|---|
| | | | | | TEA | MEA | DEE | Other | C$^2$= | | |
| 24 | 5 | CaCuHAP-1.7 | 300 | 41 | 88 | 4 | 4 | 2 | 2 | 160 | 730 |
| 25 | 5 | | 355 | 62 | 65 | 6 | 5 | 8 | 17 | 160 | 725 |
| 26 | 10 | 34% H$_3$PO$_4$/SiO$_2$ | 360 | 37 | 60 | 4 | 6 | 7 | 23 | 232 | 720 |

[a]DEA/ETOH feed molar ratio = 1
[b]TEA = triethylamine; MEA = monoethylamine; DEE = diethylether; C$^2$= = ethylene; OTHER = CPD has same retention time as NEP.
[c]GHSV = cc feed (STP)/cc catalyst/hr

TABLE III

Amination of Isopropanol with Aniline[a]

| Example | Catalyst of Example | Type | Temp °C. | Aniline Conversion % | Selectivities (mol %)[b] | | |
|---|---|---|---|---|---|---|---|
| | | | | | N | O | P |
| 27 | 2 | CaHAP-1.7 | 250 | 10 | 96 | 4 | 0 |
| 28 | 2 | | 280 | 22 | 92 | 6 | 1 |
| 29 | 2 | | 300 | 39 | 86 | 9 | 1 |
| 30 | 3 | CaHAP-1.6 | 250 | 15 | 96 | 3 | 1 |
| 31 | 5 | CaCuHAP-1.7 | 300 | 28 | 92 | 6 | 1 |

[a]P = 900 psig, aniline/isopropanol feed molar ratio = 0.5, LHSV = 0.25h$^{-1}$
[b]N = N—isopropylaniline and N,N—diisopropylaniline, O = ortho-isopropylaniline, P = para-isopropylaniline.
[c]Wt % La = 48.5; Wt % P = 12.7

TABLE IV

Amination of Ethylene Glycol (EG) with piperidine (PiPD)[a]

| Example | Catalyst Example | Type | Temp °C. | Pressure PSIG | GHSV[b] h$^{-1}$ | PiPD Conversion % | Selectivities (mol %)[c] | | | |
|---|---|---|---|---|---|---|---|---|---|---|
| | | | | | | | NHEP | BPE | NEP | OTHER |
| 32 | 2 | CaHAP-1.7 | 357 | 43 | 200 | 29 | 12 | 59 | 16 | 13 |
| 33 | 9 | AlPO$_4$-1.0 | 361 | 46 | 200 | 17 | 5 | 15 | 44 | 36 |

[a]PiPD/EG feed molar ratio = 2
[b]GHSV = cc feed/cc catalyst/hr where cc feed calculated at reaction T and P.
[c]NHEP = N—hydroxyethylpipD, BPE = bis-piperidinoethane, NEP = N—ethylpipD, Other = ethylpyridines, etc.
[d]Catalyst of Example 11 calcined at 400° C. for 8 hr in zero grade air. The temperature ramp was 2° C./min to 400° C.

The following procedure was used to test the above-mentioned catalysts in amination reactions as enumerated in examples 11 through 33. In examples 11 through 26, 14cc of 10-16 mesh catalyst was loaded into a 9/16" diameter stainless steel reactor. In examples 27 through 31, 10 cc of catalyst was used and in examples 32-33, 1 to 4 cc of catalyst was used. The reactor was placed in a conventional tube furnace such that the catalyst bed was centrally and uniformly heated to constant temperature.

In examples 11 through 33 the reactor was first presurized with the amine/alcohol feed mixture, except examples 21, 26, 32 and 33 wherein the reactor was pressurized after heating to the disclosed reaction temperature. The catalyst bed was raised to the final temperature with the feed mixture flowing at a rate such that the desired LHSV or GHSV was obtained. Product samples were collected during the run and analyzed by well established gas chromatographic techniques.

The results presented in Tables I through IV show that non-acidic hydroxyapatite catalysts as synthesized and/or calcined, demonstrate an unusual ability to selectively aminate alcohols and diols to their respective condensation product(s) in high conversion. For example, Table I discloses reaction products obtained from amination of ethanol with piperidine over calcium hydroxyapatite, alumina and H$_3$PO$_4$ catalysts. The calcium hydroxyapatite catalysts of examples 11 through 17 exhibit selectivities of greater than 99 mol % toward N-ethylpiperidine (NEP) as compared to aluminum phosphate (example 20) which yields 85 mol % NEP and a mixture of ring substituted ethyl piperidines, ring substituted diethyl piperidines and diethyl ether as by-products. Additionally, phosphate on silica or alumina (examples 21 and 22) yield 80 mol % and 83 mol % NEP, respectively Percentage conversion from piperidine to N-ethyl piperidine is shown to be greatly affected by reaction temperature with highest conversion occurring in the temperature range of about 350° to about 360° C.

More important, examples 11-19 of Table I clearly demonstrate the enhanced selectivity afforded by hydroxyapatite catalysts as compared to AlPO$_4$, H$_3$PO$_4$/SiO$_2$, H$_3$PO$_4$4/Al$_2$O$_3$ and Cu/Al$_2$O$_3$ (Examples 20-23).

It is apparent that substantial time and energy savings can be achieved by using non-acidic cationic hydroxyapatite catalysts wherein side reactions and by-products are kept to a minimum thereby eliminating complex separation of product mixtures.

Results for amination of ethanol with diethylamine are disclosed in Table II. Examples 25 and 26 demonstrate that under similar reaction conditions (temperature and pressure) the calcium hydroxyapatite catalyst having a calcium/phosphate ratio of 1.7 results in much higher conversion from diethylamine to triethylamine as compared to the 34% H$_3$PO$_4$/SiO$_2$ catalyst (62% versus 37%. respectively). Additionally, the calcium/copper hydroxyapatite catalyst of example 25 afforded greater conversion and selectivity toward triethylamine at a lower reaction temperature than the H$_3$PO$_4$/SiO$_2$ catalyst of Example 26.

Table III illustrates the amination of isopropanol with aniline wherein calcium hydroxyapatite and calcium copper hydroxyapatite are shown to be highly selective toward N-isoproplaniline and N,N-diisopropylaniline. Examples 27 through 30 demonstrate that while the percentage conversion of aniline to N-isopropylaniline increases with increasing temperature, selectivity toward the N-substituted product remains relatively constant.

Table IV discloses products obtained by amination of ethylene glycol with piperidine. Comparison of examples 32 and 33 shows that under similar reaction conditions, the calcium hydroxyapatite catalyst yields a higher conversion of piperidine to bis-piperidinoethane (59% versus 15%, respectively) as compared to the acidic AlPO$_4$ catalyst of the prior art. Moreover, AlPO$_4$ shows only 20% selectivity (versus 71 mol % selectivity of the hydroxyapatite catalyst) toward N-hydroxyethylpiperidine and bis-piperidinoethane and yields substantial amounts of dehydration products.

Without being bound to a particular theory, Applicants believe that use of non-acidic catalysts eliminates formation of certain reaction intermediates which decompose on the catalyst surface to form coke and undesirable by-products thereby reducing the yield of the desired N-alkylated product. It will be apparent to those skilled in the art that process parameters under which these catalysts operate may be adjusted to reduce undesirable side reactions while increasing product selectivity and conversion of product.

Hydroxyapatite catalysts can be successfully employed in a process for producing both cyclic and acyclic amines with substantially greater selectivity than catalysts known in the art. Additionally, non-acidic cationic hydroxapatite catalysts demonstrate higher selectivity at comparable conversion rates for amination reactions than typical acidic phosphates such as SrHPO$_4$ or La$^2$(HPO$_4$)$_3$.

Having thus described the present invention, what is now deemed appropriated for Letters Patent of the United States is set out in the following appended claims.

What is claimed is:

1. A process for the catalytic amination of a 1° or 2° alcohol or diol with a 1° or 2° amine which comprises passing a mixture of the amine and the alcohol or diol at an elevated temperature over a catalyst comprising a non-acidic cationic hydroxyapatite.

2. A process for the catalytic amination of a 1° or 2° alcohol or diol with a 1° or 2° amine which comprises passing a mixture of the amine and the alcohol or diol at an elevated temperature over a catalyst comprising a non-acidic cationic hydroxyapatite represented by the formula:

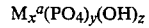
$$M_x{}^a(PO_4)_y(OH)_z$$

wherein M$^a$ is a cation selected from the group consisting of Ca$^{2+}$, Mg$^{2+}$, Sr$^{2+}$, La$^{3+}$, Ce$^{3+}$, Fe$^{2+}$, Cu$^{2+}$, Zn$^{2+}$, Al$^{3+}$, B$^{3+}$ and Ga$^{3+}$ and wherein the cation to phosphorus ratio, x/y, ranges from about 1.3 to about 2.4, calculated when a is 2+ and from about 0.87 to about 1.6 when a is 3+ and the ratio of z/y is about 1 to 3.

3. The process as defined in claim 2 wherein said catalyst contains up to about 5 wt. % of an alkali ion selected from the group consisting of lithium, sodium, potassium, rubidium or cesium.

4. The process as defined in claim 2 wherein said catalyst cation is a mixture of cations selected from the group consisting of Ca$^{2+}$, Mg$^{2+}$, Sr$^{2+}$, La$^{3+}$, Ce$^{3+}$, Fe$^{2+}$, Cu$2+$, Zn$^{2+}$, Al$^{3+}$, B$^{3+}$ and Ga$^{3+}$ wherein at least 50% of the cations in said catalyst comprises a mixture of at least two of said cations.

5. A process for the catalytic amination of a 1° or 2° alcohol or diol with a 1° or 2° amine which comprises passing a mixture of the amine and the alcohol or diol at an elevated temperature over a catalyst comprising a non-acidic cationic hydroxyapatite represented by the formula:

$$Ca_x{}^{2+}(PO_4)_y(OH)_z$$

wherein the cation to phosphorus ratio, x/y, is from about 1.67 to about 2.4 and the ratio of z/y is about 0.33 to about 1.79.

6. The process as defined in claim 5 wherein said catalyst contains up to about 5 wt. % of an alkali ion selected from the group consisting of lithium sodium, potassium, rubidium or cesium.

7. The process as defined in claim 5 wherein said amine is diethylamine and said alcohol is ethanol.

8. The process as defined in claim 5 wherein sad amine is piperidine and said alcohol is ethanol.

9. The process as defined in claim 5 wherein said amine is aniline and said alcohol is isopropanol.

10. The process as defined in claim 5 wherein said amine is piperidne and said alcohol is ethylene glycol.

11. The process as defined in claim 5 wherein said catalyst has a calcium to phosphorus ratio, x/y, of about 1.3 to 1.67 wherein said catalyst is pre-calcined with an inert gas or with steam at a temperature from about 500° to about 650° C. for an amount of time sufficient to render the pH of said catalyst non-acidic.

12. The process as defined in claim 5 wherein said catalytic amination reaction is run as a vapor phase reaction wherein said elevated temperature ranges from about 150° to about 350° C. and said pressure ranges from about 1 to 100 atmospheres.

13. The process as defined in claim 5 wherein said catalytic amination reaction is run as a liquid phase reaction wherein said elevated temperature ranges from about 100° to about 500° C.

* * * * *